(12) United States Patent
Okuda et al.

(10) Patent No.: US 7,897,333 B2
(45) Date of Patent: Mar. 1, 2011

(54) REAGENT FOR MEASURING CLOTTING TIME AND METHOD FOR MANUFACTURING THE REAGENT

(75) Inventors: Masahiro Okuda, Kobe (JP); Tomokuni Taniguchi, Yawata (JP); Masayuki Yuki, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/940,008

(22) Filed: Nov. 14, 2007

(65) Prior Publication Data

US 2008/0124704 A1 May 29, 2008

(30) Foreign Application Priority Data

Nov. 14, 2006 (JP) .................................. 2006-308061

(51) Int. Cl.
*C12Q 1/56* (2006.01)
(52) U.S. Cl. ............................................. 435/5; 435/13
(58) Field of Classification Search ........................ None
See application file for complete search history.

(56) References Cited

U.S. PATENT DOCUMENTS

| 5,314,695 A * | 5/1994 | Brown ........................... 424/450 |
| 5,625,036 A | 4/1997 | Hawkins et al. |
| 6,261,803 B1 | 7/2001 | Zander et al. |
| 7,084,251 B1 | 8/2006 | Lawn et al. |
| 2006/0046309 A1 | 3/2006 | Morrissey et al. |

FOREIGN PATENT DOCUMENTS

| EP | 1418435 A1 | 5/2004 |
| WO | 93/07492 A1 | 4/1993 |
| WO | 98/48283 A1 | 10/1998 |
| WO | 2006/096345 A2 | 9/2006 |

OTHER PUBLICATIONS

Takayenoki et al. (Biochemical and Biophysical Research Communications, vol. 181, 1991, pp. 1145-1150).*
Yoko Takayenoki et al., cDNA and Amino Acid Sequences of Bovine Tissue Factor, Biochemical and Biophysical Research Communications, Dec. 31, 1991, pp. 1145-1150, vol. 181, No. 3, Academic Press, Inc.
Cheryl L. Brucato et al., Expression of recombinant rabbit tissue factor in *Pichia pastoris*, and its application in a prothrombin time reagent, Protein Expression & Purification, 2002, pp. 386-393, vol. 26, Elsevier Science.
Kost, Thomas A. et al, "Baculovirus as versatile vectors for protein expression in insect and mammalian cells", Nature Biotechnology vol. 23, No. 5, May 2005, pp. 567-575.

* cited by examiner

*Primary Examiner* — Hope A Robinson
(74) *Attorney, Agent, or Firm* — Sughrue Mion, PLLC

(57) ABSTRACT

A reagent for measuring clotting time is described. The reagent comprises a complex of a phospholipid and a recombinant tissue factor obtained by using an insect or a cultured insect cell as a host; and a soluble component derived from the insect or the cultured insect cell.

A method for manufacturing the reagent is also described.

11 Claims, 4 Drawing Sheets

SEQUENCE LISTING

```
<160> NUMBER OF SEQ ID NOS: 6

<210> SEQ ID NO 1
<211> LENGTH: 257
<212> TYPE: PRT
<213> ORGANISM: Bos taurus

<400> SEQUENCE: 1

Thr Asp Val Val Val Ala Tyr Asn Ile Thr Trp Lys Ser Thr Asn Phe
1               5                   10                  15

Lys Thr Ile Leu Glu Trp Glu Pro Lys Pro Ile Asn His Val Tyr Thr
            20                  25                  30
```

Val Gln Ile Ser Pro Arg Leu Gly Asn Trp Lys Asn Lys Cys Phe Tyr
            35                  40                  45

Thr Thr Asn Thr Glu Cys Asp Val Thr Asp Glu Ile Val Lys Asn Val
 50                  55                  60

Arg Glu Thr Tyr Leu Ala Arg Val Leu Ser Tyr Pro Ala Asp Thr Ser
 65                  70                  75                  80

Ser Ser Thr Val Glu Pro Pro Phe Thr Asn Ser Pro Glu Phe Thr Pro
                 85                  90                  95

Tyr Leu Glu Thr Asn Leu Gly Gln Pro Thr Ile Gln Ser Phe Glu Gln
                100                 105                 110

Val Gly Thr Lys Leu Asn Val Thr Val Gln Asp Ala Arg Thr Leu Val
                115                 120                 125

Arg Ala Asn Ser Ala Phe Leu Ser Leu Arg Asp Val Phe Gly Lys Asp
    130                 135                 140

Leu Asn Tyr Thr Leu Tyr Tyr Trp Lys Ala Ser Ser Thr Gly Lys Lys
145                 150                 155                 160

Lys Ala Thr Thr Asn Thr Asn Gly Phe Leu Ile Asp Val Asp Lys Gly
                    165                 170                 175

Glu Asn Tyr Cys Phe His Val Gln Ala Val Ile Leu Ser Arg Arg Val
                180                 185                 190

Asn Gln Lys Ser Pro Glu Ser Pro Ile Lys Cys Thr Ser His Glu Lys
    195                 200                 205

Val Leu Ser Thr Glu Leu Phe Phe Ile Ile Gly Thr Val Met Leu Val
    210                 215                 220

Ile Ile Ile Phe Ile Val Val Leu Ser Val Ser Leu His Lys Cys Arg
225                 230                 235                 240

Lys Val Arg Ala Glu Arg Ser Gly Lys Glu Asn Thr Pro Leu Asn Ala
                245                 250                 255

Ala

<210> SEQ ID NO 2
<211> LENGTH: 292
<212> TYPE: PRT
<213> ORGANISM: Bos taurus

<400> SEQUENCE: 2

Met Ala Thr Pro Asn Gly Pro Arg Val Pro Cys Pro Gln Ala Ala Val
 1               5                  10                  15

Ala Arg Ala Leu Leu Phe Gly Leu Val Leu Ile Gln Gly Ala Gly Val
                 20                  25                  30

Ala Gly Thr Thr Asp Val Val Val Ala Tyr Asn Ile Thr Trp Lys Ser
            35                  40                  45

Thr Asn Phe Lys Thr Ile Leu Glu Trp Glu Pro Lys Pro Ile Asn His
 50                  55                  60

Val Tyr Thr Val Gln Ile Ser Pro Arg Leu Gly Asn Trp Lys Asn Lys
 65                  70                  75                  80

Cys Phe Tyr Thr Thr Asn Thr Glu Cys Asp Val Thr Asp Glu Ile Val
                 85                  90                  95

Lys Asn Val Arg Glu Thr Tyr Leu Ala Arg Val Leu Ser Tyr Pro Ala
                100                 105                 110

Asp Thr Ser Ser Ser Thr Val Glu Pro Pro Phe Thr Asn Ser Pro Glu
            115                 120                 125

Phe Thr Pro Tyr Leu Glu Thr Asn Leu Gly Gln Pro Thr Ile Gln Ser
130                 135                 140

-continued

Phe Glu Gln Val Gly Thr Lys Leu Asn Val Thr Val Gln Asp Ala Arg
145                 150                 155                 160

Thr Leu Val Arg Ala Asn Ser Ala Phe Leu Ser Leu Arg Asp Val Phe
            165                 170                 175

Gly Lys Asp Leu Asn Tyr Thr Leu Tyr Tyr Trp Lys Ala Ser Ser Thr
        180                 185                 190

Gly Lys Lys Lys Ala Thr Thr Asn Thr Asn Gly Phe Leu Ile Asp Val
    195                 200                 205

Asp Lys Gly Glu Asn Tyr Cys Phe His Val Gln Ala Val Ile Leu Ser
210                 215                 220

Arg Arg Val Asn Gln Lys Ser Pro Glu Ser Pro Ile Lys Cys Thr Ser
225                 230                 235                 240

His Glu Lys Val Leu Ser Thr Glu Leu Phe Phe Ile Ile Gly Thr Val
                245                 250                 255

Met Leu Val Ile Ile Ile Phe Ile Val Val Leu Ser Val Ser Leu His
            260                 265                 270

Lys Cys Arg Lys Val Arg Ala Glu Arg Ser Gly Lys Glu Asn Thr Pro
        275                 280                 285

Leu Asn Ala Ala
    290

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 3
agatctatgg cgaccccaa cgggcc                                    26

<210> SEQ ID NO 4
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 4
acttaagaat acgtcgcaac tcgccgc                                  27

<210> SEQ ID NO 5
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 5
ggatccatgg cgaccccaa cgggccccg                                 29

<210> SEQ ID NO 6
<211> LENGTH: 28
<212> TYPE: DNA
<213> ORGANISM: Artificial
<220> FEATURE:
<223> OTHER INFORMATION: Synthetic oligonucleotide primer

<400> SEQUENCE: 6
ctcgagttat gcagcgttga gcggcgtg                                 28

REAGENT FOR MEASURING CLOTTING TIME AND METHOD FOR MANUFACTURING THE REAGENT

CROSS-REFERENCE TO RELATED APPLICATION

This application claims foreign priority to JP 2006-308061, filed Nov. 14, 2006; the disclosure of which is incorporated in its entirety by reference.

BACKGROUND OF THE INVENTION

1. Field of the Invention

The present invention relates to a reagent for coagulation test used in examination of the extrinsic clotting system of blood and a method for manufacturing the reagent.

2. Description of the Related Art

Thromboplastin is a complex between a protein called tissue factor and phospholipid. Thromboplastin is involved in blood coagulation. Hence, thromboplastin has been utilized in various coagulation tests. For example, a reagent for thrombo-test for comprehensively examining the coagulation ability of factors II, VII and X (or factors II, VII, IX and X) in blood contains bovine brain tissue thromboplastin, fibrinogen, factor V, calcium and phospholipid.

Bovine brain tissue thromboplastin as a major component in the reagent for thrombo-test is a complex having a phospholipid added to a protein called tissue factor. The tissue factor is a protein consisting of 257 amino acids in total as shown in FIG. 3 in Yuko Takayenoki et al.: "cDNA and amino acid sequences of bovine tissue factor", Biochemical and Biophysical Research Communications, Vol. 181, 1991, pages 1145-1150. The tissue factor consists of an extracellular domain (soluble domain) of from the N-terminal to amino acid 213, a transmembrane domain of from amino acid 214 to amino acid 236 and an intracellular domain of from amino acid 237 to amino acid 257.

Conventionally, thromboplastin having such constitution has been produced by extracting thromboplastin from a bovine cerebrum as a starting material with acetone powder or physiological saline.

A bovine cerebrum used as a starting material is one site affected highly with bovine spongiform encephalopathy (BSE). Hence, there is recently demand for a manufacturing method without using a bovine cerebrum as a starting material.

There are reports on manufacturing, by utilizing genetic engineering techniques, of a recombinant tissue factor having an activity as a composition of a measurement reagent. Examples of such reports include WO 93/07492, WO 98/48283, and a literature of Cheryl L Brucatol et al. ("Expression of recombinant rabbit tissue factor in *Pichia pstoris*, and its application in a prothrombin time reagent", Protein Expression and Purification, Vol. 26, 2002, pages 386-393).

Specifically, in WO 93/07492 supra, a recombinant human tissue factor is expressed in *Escherichia coli*. Then, the recombinant human tissue factor is purified by affinity chromatography with an immobilized monoclonal antibody to human tissue factor. Then, the purified recombinant human tissue factor is applied to a prothrombin reagent.

In the literature of Cheryl L Brucatol et al., a recombinant rabbit tissue factor (rTF) is expressed in yeasts. Then, a histidine tag is used to purify rTF, and the resulting rTF is applied to a prothrombin time reagent. In this literature, it is reported that the expressed rabbit tissue factor is a full-length tissue factor consisting of an intracellular domain, a transmembrane domain and an extracellular domain.

In WO 98/48283, a full-length recombinant rabbit tissue factor consisting of an extracellular domain, a lipid-bound domain and an intracellular domain is expressed in yeasts. Then, a histidine tag specifically enriching the recombinant tissue factor is utilized to purify the recombinant rabbit tissue factor. Then, the purified rabbit tissue factor is applied to a prothrombin time reagent.

As described above, a recombinant tissue factor purified by chromatography etc. is used in order to prevent the reduction in the coagulation activity of a reagent, or the reduction in measurement accuracy, caused by contamination of the reagent with host-derived impurities. For purification of the recombinant tissue factor, however, it is necessary to construct a system for efficiently separating and removing host-derived impurities. When the recombinant tissue factor is produced in a large amount, the step of purifying it requires considerable time, labor, cost etc., and thus there is a problem in productivity of the recombinant tissue factor.

In the purification method using affinity chromatography with a specific antibody, for example, use of the specific antibody causes higher costs in mass production.

For the recombinant rabbit tissue factor, for example, the purification method using affinity chromatography with a histidine tag has been practically used as a purification method suited to mass production. However, the linking of a histidine tag to the recombinant tissue factor may exert an influence on coagulation activity, depending on the type of host or the type of tissue factor. In this purification method, therefore, the histidine tag is cut off after purification. Addition of this step of cutting the tag off leads to an increase in production costs.

Depending on the steric structure of tissue factor, the tissue factor may not be successfully purified even by chromatography with a histidine tag.

From the foregoing, a production system capable of satisfying productivity with respect to costs and quantity of production without influencing coagulation activity should be constructed for production of the tissue factor by genetic engineering techniques. It is then desired to provide a reagent for measuring clotting time using a tissue factor obtained by the constructed production system.

SUMMARY OF THE INVENTION

The scope of the present invention is defined solely by the appended claims, and is not affected to any degree by the statements within this summary.

A first aspect of the present invention is a reagent for measuring clotting time, comprising: a complex of a phospholipid and a recombinant tissue factor obtained by using an insect or a cultured insect cell as a host; and a soluble component derived from the insect or the cultured insect cell.

A second aspect of the present invention a method for manufacturing a reagent for measuring clotting time, comprising the steps of: infecting an insect or a cultured insect cell with a recombinant baculovirus obtained by integrating tissue factor cDNA in baculovirus DNA; expressing a recombinant tissue factor encoded by the cDNA, in the insect or the cultured insect cell; preparing a soluble composition containing the recombinant tissue factor by removing insoluble materials from a solution containing disrupted materials obtained by disrupting the insect or the cultured insect cell having expressed the recombinant tissue factor; and forming a complex of the recombinant tissue factor and a phospholipid by mixing the soluble composition with the phospholipid.

DESCRIPTION OF THE PREFERRED EMBODIMENTS

Figure 1:
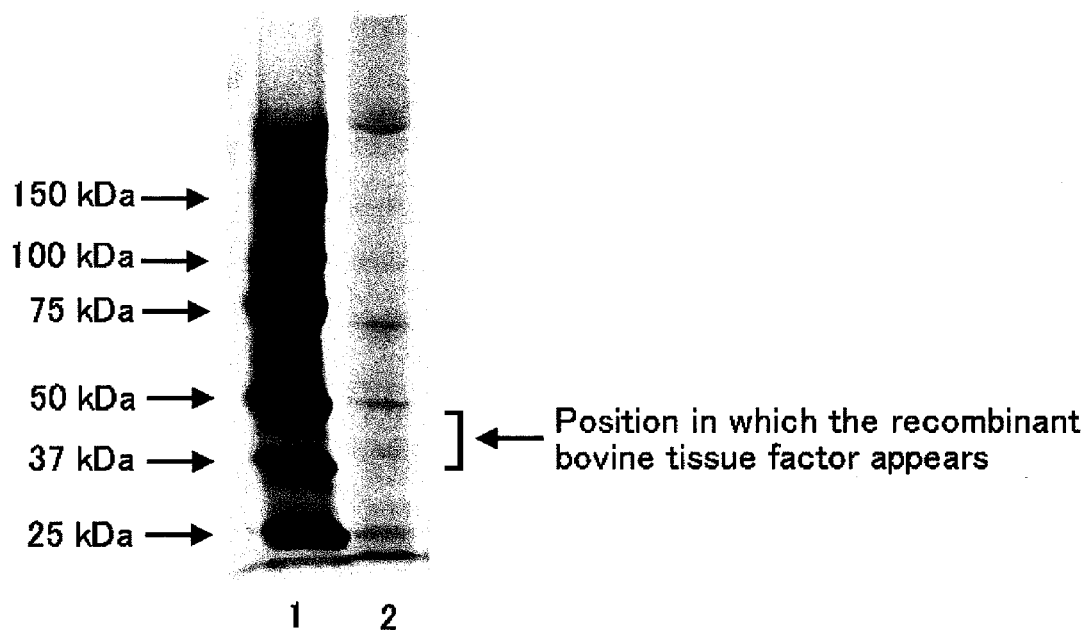
FIG. 1 shows SDS-PAGE results of a recombinant bovine tissue factor-containing solution SW.

The reagent for measuring clotting time in one embodiment of the invention comprises a complex of a phospholipid and a recombinant tissue factor obtained by using an insect or a cultured insect cell as a host, and a soluble component derived from the insect or the cultured insect cell.

The reagent for measuring clotting time contains a recombinant tissue factor produced by genetic engineering techniques, and further contains soluble components derived from an insect or a cultured insect cell used as the host. However, the reagent can show coagulation activity and sensitivity comparable to those of conventional reagents for measuring clotting time contain native thromboplastin.

The reagent for measuring clotting time makes use of a recombinant tissue factor in place of native thromboplastin, thereby eliminating the necessity for dealing on the spot with the cerebrum at the root of BSE etc., and is thus safe. Further, the method for manufacturing the reagent for measuring clotting time can simplify a step of purifying the recombinant tissue factor, and is thus excellent in productivity and can achieve a reduction in production costs.

Recombinant Tissue Factor and Phospholipid Complex of the Tissue Factor

First, a recombinant tissue factor used in the reagent for measuring clotting time, and a complex of the recombinant tissue factor and a phospholipid (hereinafter also referred to as rTF-PL complex), are described.

The recombinant tissue factor is obtained by genetic engineering techniques with an insect or a cultured insect cell as the host. The recombinant tissue factor includes a recombinant bovine tissue factor, a recombinant rabbit tissue factor and a recombinant human tissue factor obtained by such genetic engineering techniques.

Native tissue factor is conjugated with a phospholipid thereby activating factor VII in human blood. Therefore, the recombinant tissue factor preferably has at least a soluble domain and transmembrane domain of native tissue factor. The soluble domain of recombinant tissue factor is a domain necessary for interaction with factor VII, and the transmembrane domain is a domain necessary for formation of a complex with phospholipid.

The recombinant tissue factor is more preferably one having a soluble domain, a transmembrane domain and an intracellular domain in such a range that the ability of the tissue factor to form a complex with phospholipid and activate factor VII is not deteriorated. Such recombinant bovine tissue factor is, for example, a tissue factor which has an amino acid sequence represented by SEQ ID NO: 1 or an amino acid sequence derived from the amino acid sequence of SEQ ID NO: 1 by substitution, addition or deletion of one or more amino acids and which forms a complex with phospholipid to activate factor VII. Specifically, a recombinant tissue factor having at least 95% sequence homology with the amino acid sequence represented by SEQ ID NO: 1 is preferable, a recombinant tissue factor having at least 97% sequence homology is more preferable, and a recombinant tissue factor having at least 99% sequence homology is most preferable.

Figure 3:
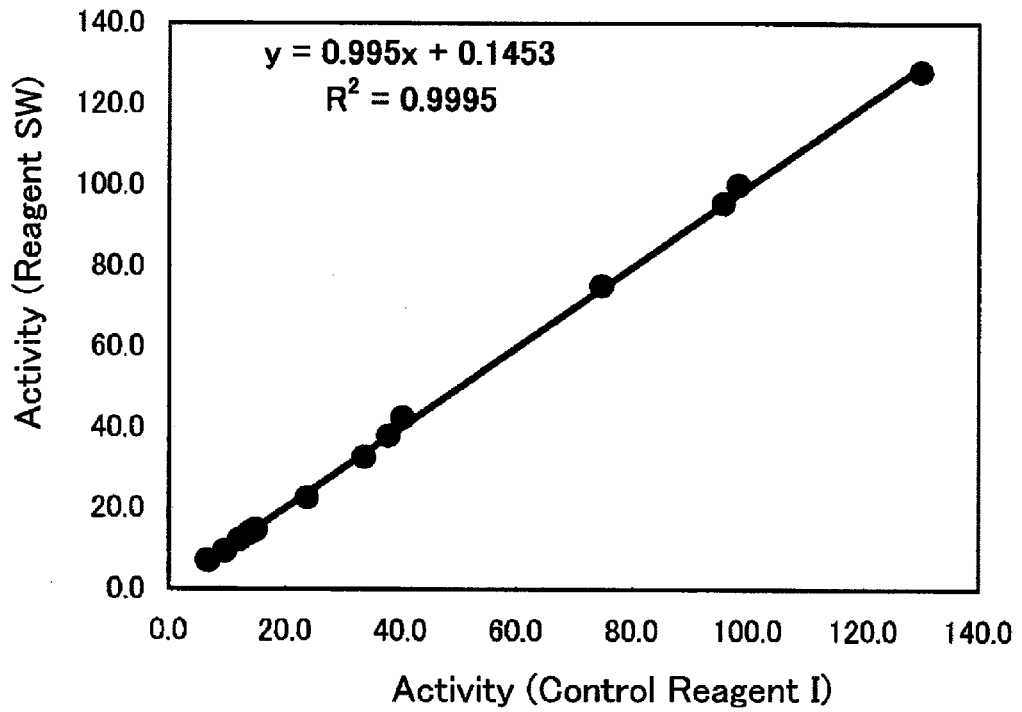
FIG. 3 is a graph showing the relationship between the activity of a control reagent I and the activity of a reagent SW.

SEQ ID NO: 1 shows an amino acid sequence of normal bovine tissue factor shown in FIG. 3 in the literature of Yuko Takayenoki et al. supra. That is, in SEQ ID NO: 1, a region of from amino acid 1 to amino acid 213 corresponds to a soluble domain (extracellular domain), a region of from amino acid 214 to amino acid 236 corresponds to a transmembrane domain, and a region of from amino acid 237 to amino acid 257 corresponds to an intracellular domain.

The recombinant tissue factor as described above is obtained by genetic engineering techniques with an insect or a cultured insect cell as the host. This will be described later in detail.

The rTF-PL complex has a phospholipid bound to a transmembrane domain of the recombinant tissue factor, and has a blood coagulation activity at the same level as that of native thromboplastin (native tissue factor of phospholipid complex type). Such complex can be produced by mixing the recombinant tissue factor with a phospholipid by utilizing a known method. For example, the complex can be produced by methods described in WO 93/07492, WO 98/48283, and the above-mentioned literature of Cheryl L Brucatol et al.

The phospholipid used in forming the complex is generally preferably a phospholipid containing a C12 to C22 fatty acid. The fatty acid may be a saturated or unsaturated fatty acid. Preferable phospholipids are exemplified specifically by phosphatidyl choline, phosphatidyl ethanolamine, phosphatidyl glycerol and phosphatidyl serine. These phospholipids may be natural products or synthetic products. These phospholipids may be those having different kinds of fatty acids. Prior to use in forming the complex, two or more of these phospholipids may be mixed depending on desired states and characteristics.

Reagent for Measuring Clotting Time

The reagent for measuring clotting time in one embodiment of the present invention contains soluble components derived from an insect or a cultured insect cell as the host used in obtaining the rTF-PL complex or the recombinant tissue factor.

The recombinant tissue factor contained in the reagent for measuring clotting time is obtained by genetic engineering techniques with an insect or a cultured insect cell as the host. Soluble components in an insect or a cultured insect cell used as the host will be extracted together with the recombinant tissue factor from the host, and thus the soluble components are eventually contained together with the recombinant tissue factor in the reagent for measuring clotting time.

The type of insect used as the host is not limited. As an insect used as the host, a lepidopteran insect is preferably used. The lepidopteran insect is preferably a silkworm (scientific name: *Bombyx mori*).

The cultured insect cell used as the host includes Sf9, Sf21 and HiFive, among which Sf9 is preferably used.

When the recombinant tissue factor is extracted from the host, the insect or the cultured insect cell as host are disrupted in water or a suitable solution such as a buffer. From the solution containing disrupted materials obtained by disruption, insoluble materials are removed by filtration or centrifugation. Soluble components derived from the insect or the cultured insect cell are those components which can be contained in a filtrate obtained by removing insoluble materials by filtration from the solution containing disrupted materials of the insect or the cultured insect cell, or those components which can be contained in a supernatant obtained by removing insoluble materials by centrifugation from the solution containing disrupted materials of the insect or the cultured insect cell. Examples of soluble components include components dissolved in a body fluid of the insect or components dissolved in the cytosol of the cultured insect cell. Specific examples include soluble proteins constituting the insect or the cultured insect cell, water-soluble sugar chains, and soluble proteins produced by the insect or the cultured insect cell.

The reagent for measuring clotting time contains the above rTF-PL complex and the above soluble components of the insect or the cultured insect cell. Further, the reagent may appropriately contain a coagulation factor, a calcium ion, a phospholipid etc. depending on the type of the reagent for measuring clotting time (that is, the type of the coagulation factor to be examined).

For example, when the reagent is a reagent for thrombo-test that is a test for comprehensively examining the coagulation ability of factors II, VII and X (or factors II, VII, IX and X), the reagent contains the recombinant bovine tissue factor-phospholipid complex and soluble components of the insect or the cultured insect cell. Preferably, the reagent further contains factors I and V and a calcium ion as other components. In place of factors I and V to be added, plasma from which factors II, VII and X (or factors II, VII, IX and X) were removed may be used. As the plasma, barium sulfate-adsorbed plasma obtained by adsorbing plasma (preferably bovine plasma) with barium sulfate is preferably used. Barium sulfate-adsorbed plasma can be prepared by adding barium sulfate to plasma (preferably bovine plasma), mixing them and removing the barium sulfate. The reagent for thrombo-test is also referred to as "a thrombo-test reagent" or "II-VII-X reagent".

When the reagent is a reagent for hepaplastin test that is a test for comprehensively examining the coagulation ability of factors II, VII and X, the reagent contains the recombinant rabbit tissue factor-phospholipid complex and soluble components of the insect or the cultured insect cell. Preferably, the reagent further contains factors I and V and a calcium ion as other components. In place of factors I and V to be added, the plasma as described above from which factors II, VII and X (or factors II, VII, IX and X) were removed may be used.

When the reagent is a prothrombin time reagent, the reagent contains the recombinant rabbit tissue factor-phospholipid complex or the recombinant human tissue factor-phospholipid complex and soluble components of the insect or the cultured insect cell. Preferably, the reagent further contains a calcium ion as another component.

A source of the calcium ion is usually selected from calcium chloride, calcium lactate and calcium gluconate.

If necessary, a buffer selected from the group consisting of HEPES, TRIPS, MOPS, PIPES, BISTRIS, and Glycine may be contained in the reagent such that the pH reaches 5 to 9, and the final concentration reaches about 10 to 100 mM.

The reagent for measuring clotting time having the composition as described above contains soluble components derived from an insect or a cultured insect cell. Nevertheless, the reagent for measuring clotting time has a coagulation activity comparable to that of a reagent using native thromboplastin. When the reagent for measuring clotting time is a reagent for thrombo-test which contains the recombinant bovine tissue factor-phospholipid complex, the reagent for measuring clotting time has such sensitivity to PIVKA (protein induced in vitamin K absence or antagonists) as to be comparable to that of a reagent for thrombo-test which contains native bovine thromboplastin. Therefore, the reagent for measuring clotting time can also be used as a reagent used for monitoring the therapeutic effect of warfarin or the like.

The term "PIVKA" refers generically to precursors free of normal coagulation factor activity. PIVKA appears in blood in vitamin K deficiency or in the presence of vitamin K antagonists. Among blood coagulation factors, factors II, VII, IX and X, for example, are synthesized in the liver. In the final stage of their synthesis, vitamin K is necessary. It follows that in vitamin K deficiency or at the time of administration of vitamin K inhibitors such as warfarin, these factors will appear in blood in the form of precursors free of normal coagulation factor activity. It is reported that bovine tissue factor is highly sensitive to PIVKA, while rabbit tissue factor and human tissue factor are low in sensitivity to PIVKA (see Hemker et al., "Kinetic aspects of the interaction of blood clotting enzymes, III. Demonstration of an inhibitor of prothrombin conversion in vitamin K deficiency," Thromb Diath Haemorrh, Vol. 19, pages 346-363, 1968); and Denson K. W., Reed S. V., Haddon M. E., "Validity of the INR system for patients with liver impairment, " Thromb Haemost, Vol. 73, page 162, 1995). For this reason, the reagent for thrombo-test which contains bovine tissue factor, is used at present for monitoring the therapeutic effect of warfarin or the like. A test using the reagent for thrombo-test which contains bovine tissue factor is also called a thrombo-test.

Method for Manufacturing Reagent for Measuring Clotting Time

The method for manufacturing a reagent for measuring clotting time comprises the steps of: infecting an insect or a cultured insect cell with a recombinant baculovirus obtained by integrating tissue factor cDNA in baculovirus DNA; expressing a recombinant tissue factor encoded by the cDNA, in the insect or the cultured insect cell; removing insoluble materials from a solution containing disrupted materials obtained by disrupting the insect or the cultured insect cell having expressed the recombinant tissue factor, thereby preparing a soluble composition containing the recombinant tissue factor; and mixing the soluble composition with a phospholipid, thereby forming a complex of the recombinant tissue factor and the phospholipid.

The tissue factor cDNA used in the manufacturing method is cDNA for a tissue factor used in the objective reagent for measuring clotting time. The tissue factor cDNA has at least a nucleotide sequence encoding a soluble domain and a nucleotide sequence encoding a transmembrane domain. Preferably the tissue factor cDNA has a nucleotide sequence capable of encoding soluble, transmembrane and intracellular domains of the tissue factor. In the case of bovine tissue factor, for example, it is preferable to use a nucleotide sequence capable of encoding the amino acid sequence (AAB20755) represented by SEQ ID NO: 2 or a nucleotide sequence capable of encoding an amino acid sequence derived from this amino acid sequence by substitution, addition or deletion of one or more amino acids. Specifically, the nucleotide sequence is preferably a nucleotide sequence encoding an amino acid sequence having at least 95% homology to the amino acid sequence represented by SEQ ID NO: 2, more preferably a nucleotide sequence encoding an amino acid sequence having at least 97% homology thereto, most preferably a nucleotide sequence encoding an amino acid sequence having at least 99% homology thereto. More specifically, bovine tissue factor cDNA available from cDNA library etc. of Clontech Laboratories, Inc. or Stratagene Corporation can be used.

Such cDNA is integrated in baculovirus DNA to prepare a recombinant baculovirus.

Baculovirus has a cyclic double-stranded DNA as gene. Baculovirus is a virus pathogenic for insect. Baculovirus includes nucleopolyhedrovirus (NPV) and geanulovirus (GN). The baculovirus used is preferably NPV. NPV is a virus which in an injected cell, synthesizes a protein called polyhedrin. A gene encoding this polyhedrin protein is not necessary for growth of baculovirus. The objective tissue factor can be synthesized in infected cells by inserting, downstream of a promoter of the polyhedrin gene, the cDNA of the objective tissue factor in place of the polyhedrin gene.

A baculovirus made artificially deficient in a cysteine protease gene is preferably used to eliminate the influence of proteolysis by cysteine protease produced by the virus.

A recombinant baculovirus into which the tissue factor cDNA was introduced can be created by known recombinant technology. For example, the tissue factor cDNA is inserted into a baculotransfer vector. An insect cell is cotransfected with the resulting transfer vector and a baculovirus DNA. Homologous recombination occurs in the insect cell, whereby a recombinant baculovirus having the tissue factor cDNA integrated in the baculovirus DNA can be created. When baculovirus-containing *Escherichia coli* DH10 Bac (Gibco BRL) is used, a recombinant baculovirus can be created by transfecting *E. coli* DH10 Bac with a transfer vector into which the tissue factor cDNA was inserted.

Then, a host insect or cultured insect cell is infected with the baculovirus recombinant thus prepared.

When the host is an insect, the type of insect is not particularly limited. As the insect used as a host, a lepidopteran insect is preferably used. A silkworm (*Bombyx mori*) is particularly preferable among lepidopteran insects. The type of silkworm is not particularly limited. As the silkworm, a silkworm of exarate pupa strain is preferably used. The silkworm of exarate pupa strain is a silkworm whose gene involved in cocoon formation was mutated. Therefore, the silkworm of exarate pupa strain does not form a cocoon upon pupation. Known examples of such silkworm of exarate pupa strain include silkworms of Nd strain, Ndb strain, Nd-s strain and Nd-t strain. Pupae of such silkworms are preferably used. Pupae have a significantly lower activity of serine protease for decomposing their food (mulberry leaves), occurring in alimentary tracts of silkworm larva, than that of silkworms. In the pupae, therefore, silkworm's expressed protein can be prevented from being decomposed. Silkworm pupae are more sensitive to baculovirus than silkworm larvae are. Therefore, the virus can easily multiply in silkworm pupae to express a large amount of the tissue factor.

When the host is a cultured insect cell, established cultured cells such as Sf9, Sf21 and HiFi can be used. Among these cells, Sf9 is preferable.

When a cultured insect cell is used, the tissue factor as an expressed protein product may be secreted outside of the cells or may be accumulated in the cells.

As the infection method, a known method can be used. For example, when the host is an insect, it is possible to use an injection method of injecting a viral fluid into an insect or a micro-inoculation method of inoculating an insect with a microvolume viral fluid applied onto a needle. Alternatively, cultured insect cells are transfected with the recombinant baculovirus, the resulting cultured insect cells are cultured for a predetermined period to multiply the recombinant baculovirus, and an insect is inoculated with the multiplied recombinant baculovirus, whereby the insect can be infected with the virus. When a cultured insect cell is used as the host, the cultured insect cell is cultured for a predetermined period in a culture solution containing the virus fluid, whereby the cultured insect cell can be infected with the virus.

When the host is an insect, the infected insect is raised for 5 to 10 days. During raising, the cDNA inserted into the recombinant baculovirus is expressed in the host and the objective tissue factor is produced in the insect. The produced tissue factor is accumulated in the insect. The recombinant tissue factor accumulated in the insect is thought to have undergone post translational processing through which its N-terminal is cut off. The recombinant bovine tissue factor thus processed and accumulated in the insect is, for example, the one represented by SEQ ID NO: 1. After raising for a predetermined period, the produced tissue factor is extracted from the host.

When the host is a cultured insect cell, the cultured insect cell is cultured together with the virus fluid for 2 to 7 days. During culture, the cDNA inserted into the recombinant baculovirus is expressed in the host and the objective tissue factor is produced in the cultured insect cell. The produced tissue factor is accumulated in the cultured insect cell or secreted into the medium. The recombinant tissue factor accumulated in the cultured insect cell, similar to the recombinant tissue factor accumulated in the insect, is thought to have undergone post translational processing through which its N-terminal is cutoff. The recombinant bovine tissue factor thus processed and accumulated in the cultured insect cell is, for example, the one represented by SEQ ID NO: 1. After culture for a predetermined period, the produced tissue factor is extracted from the cultured cells or the medium.

When an insect is used as the host, the tissue factor can be extracted from the insect by the following method. First, the insect which has expressed the recombinant tissue factor is disrupted. Insoluble materials are removed from the resulting solution containing disrupted materials. Soluble components containing the recombinant tissue factor can thereby be collected.

The insect can be mechanically ground with a mixer, a homogenizer, a blender or by sonication. Non-mechanical treatment with a surfactant or the like may be combined with the mechanical treatment. Disruption of the insect is carried out preferably in water or a suitable solution such as a buffer. Hereinafter, such solution is referred to as "solution for disruption treatment". The solution for disruption treatment includes, for example, water, a buffer such as phosphate buffer and Tris buffer, and a buffer containing a surfactant.

Removal of insoluble materials from the solution containing disrupted materials can be carried out by filtration, centrifugation or a suitable combination thereof.

When a cultured insect cell is used as the host, the tissue factor can be extracted from the cultured insect cell or the medium by the following method. First, the cultured cell which has expressed the recombinant tissue factor are disrupted. Insoluble materials are removed from the resulting solution containing disrupted materials. Soluble components containing the recombinant tissue factor can thereby be collected.

The cultured cell can be mechanically ground with a homogenizer or by sonication, for example. Alternatively, the cultured cell can be non-mechanically disrupted (lysed) with a surfactant or the like. Mechanical treatment can be combined with non-mechanical treatment. Disruption of the cultured cell, similar to disruption of the insect as host, is carried out preferably in a suitable solution for disruption treatment. Removal of insoluble materials from the solution containing disrupted materials can be carried out by filtration, centrifugation or a suitable combination thereof.

The disrupted material-containing solution obtained by disrupting the insect or the cultured insect cell contains a soluble composition containing the recombinant tissue factor. The soluble composition contains the recombinant tissue factor and soluble components derived from the insect or the cultured insect cell as the host. The disrupted material-containing solution also contains the baculovirus used in gene transfection, in addition to the soluble composition. A surfactant is also useful in inactivating the virus and is thus preferably used in extraction of the recombinant tissue factor. The surfactant may be a nonionic, cationic or anionic surfactant. From a virucidal viewpoint, the surfactant to be used is preferably a nonionic surfactant. Addition of the nonionic surfactant is also useful in solubilization of the recombinant tissue factor.

As described above, the solution for disruption treatment is a solution used in disrupting an insect or a cultured insect cell as the host. The solution for disruption treatment includes, for example, water, a buffer such as phosphate buffer and Tris buffer, and a buffer containing a surfactant. By disrupting the insect or the cultured insect cell in the solution for disruption treatment, the produced recombinant tissue factor and soluble components derived from the insect or the cultured insect cell are dissolved in the solution for disruption treatment.

As used herein, the soluble components derived from an insect or a cultured insect cell are components soluble in the solution for disruption treatment. It follows that even after insoluble materials are removed from the solution containing disrupted materials by filtration or centrifugation, a filtrate obtained by filtration or a supernatant obtained by centrifugation can contain the soluble components. Such soluble components derived from an insect or a cultured insect cell include, for example, components dissolved in a body fluid of the insect or in the cytosol of the cultured insect cell. Specific examples include soluble proteins constituting the insect or the cultured insect cell, water-soluble sugar chains, and soluble proteins produced by the insect or the cultured insect cell.

On the other hand, the insoluble materials are materials insoluble in the solution for disruption treatment. Specific examples include solid materials of disrupted cuticular layers and cell membranes, lipoproteins, lipids and insoluble proteins.

In this manner, insoluble materials are removed from the disrupted material-containing solution, whereby a solution freed of insoluble materials is obtained. Specific examples of the solution freed of insoluble materials include a filtrate obtained by filtering the disrupted material-containing solution and a supernatant obtained by centrifuging the disrupted material-containing solution. Then, such solution freed of insoluble materials maybe used as a solution containing the recombinant tissue factor (hereinafter referred to as "rTF-containing solution").

After removal of insoluble materials, the solution freed of insoluble materials may be dialyzed against a buffer, pH 6 to 7, such as HEPES, as an external solution. The solution freed of insoluble components, obtained after dialysis, may be used as an rTF-containing solution.

Formation of an rTF-PL complex can be carried out in a usual manner (see Methods Enzymol., 222, p. 173, 1993 etc.). Particularly, the complex is formed preferably by mixing the rTF-containing solution with a phospholipid solution in the presence of nickel.

A step of forming the rTF-PL complex can be carried out after removal of insoluble materials by filtration, centrifugation or the like. When the solution freed of insoluble materials is to be dialyzed, the step of forming the complex may be carried out either before or after dialysis. When salting-out is used, the step of forming the complex may also be carried out either before or after dialysis.

The phospholipid solution contains a phospholipid used in forming the complex. The phospholipid used is preferably a phospholipid having C12 to C22 fatty acid or unsaturated fatty acid. Specifically, the phospholipids illustrated above for the rTF-PL complex can be used. The molar ratio of the rTF-containing solution to the phospholipid solution is preferably in the range of from about $1/10$ to $1/2 \times 10^7$, more preferably in the range of from 1/3000 to 1/15000.

As nickel, an aqueous solution of a nickel salt such as nickel chloride or nickel sulfate or a solution containing a nickel salt dissolved in a buffer is used.

The rTF-containing solution, the phospholipid solution and the nickel salt solution as described above are mixed and reacted under stirring for about 1 to 2 hours, whereby an rTF-PL complex can be formed.

If the reagent for measuring clotting time to be produced contains a calcium ion, then a calcium ion source such as calcium chloride, calcium lactate or calcium gluconate is added in the manufacturing process.

If the reagent for measuring clotting time to be produced is a reagent for thrombo-test, then factors I and V are added in the manufacturing process. Instead of factors I and V to be added, plasma from which factors II, VII and X were removed (or plasma from which factors II, VII, IX and X were removed) may be used. As the plasma, barium sulfate-adsorbed plasma obtained by adsorbing plasma (preferably bovine plasma) with barium sulfate may be used. Preparation method of barium sulfate-adsorbed plasma is not particularly limited. For example, barium sulfate-adsorbed plasma can be prepared by a method of Owren et al. described by Charles et al.: "One-stage Prothrombin Time Techniques", Thrombosis and Bleeding Disorders Theory and Method, 1971, pp. 92-97).

In the manufacturing process, a buffer selected from the group consisting of HEPES, TRIPS, MOPS, PIPES, BIS-TRIS, and Glycine may be added such that the pH reaches 5 to 9, and the final concentration reaches about 10 to 100 mM.

Factors I and V (or barium sulfate-adsorbed plasma etc.), a calcium ion source, a buffer etc., which are added as necessary, may be added before or after formation of the rTF-PL complex. The order of adding factors I and V, a calcium ion source, a buffer etc. is not particularly limited.

The reagent for measuring clotting time produced in this manner contains the rTH-PL complex and components essential for the reagent for measuring clotting time. Specifically, the components essential for the reagent for measuring clotting time include a calcium ion in the case of the prothrombin time reagent. The components essential for the reagent for thrombo-test or for the reagent for hepaplastin test include calcium, factor I, and factor V. Barium sulfate-adsorbed plasma may be used in place of factors I and V. Soluble components derived from the host used in producing the recombinant tissue factor are contained in the reagent for measuring clotting time produced by the manufacturing method. The present inventors found that the soluble components from the host (the insect or the cultured insect cells) do not exert any influence on blood coagulation reaction in the test. On the basis of this finding, it is possible to provide a reagent for measuring clotting time which is substantially not problematic even if the recombinant tissue factor produced by genetic engineering techniques is not purified at high degrees by chromatography etc. in the step of extracting the recombinant tissue factor. It follows that according to the method for manufacturing the reagent for measuring clotting time, the step of purifying the recombinant tissue factor produced by genetic engineering techniques is simplified, thus achieving a reduction in production costs.

EXAMPLES

Production of Recombinant Bovine Tissue Factor by Silkworm as Host

A bovine cerebrum cDNA library (Clontech Laboratories, Inc.) was obtained, and on the basis of the method described in the literature of Yuko Takayenoki et al. supra, a gene of bovine tissue factor was amplified by PCR. A full-length bovine tissue factor-coding gene encoding a soluble domain and transmembrane domain of bovine tissue factor was cloned. In PCR amplification, a primer having a BgIII cleavage site (5'-agatctatggcgacccccaacgggcc (SEQ ID NO: 3)) was used as the forward primer, and a primer having an EcoRI cleavage site (5'-acttaagaatacgtcgcaactcgccgc (SEQ ID NO: 4)) was used as the backward primer. The cloned gene could be confirmed to be a DNA encoding a protein represented by SEQ ID NO: 2 by examining its nucleotide sequence with a sequencer (4200 type, LI-COR Inc.).

The cloned cDNA was inserted into a cloning site of cysteine protease-deficient virus pYNG (Katakura Industries Co., Ltd.) to give a recombinant baculovirus. A baculovirus expression system for expressing bovine tissue factor was established by using the recombinant baculovirus.

Silkworm pupae were infected with the recombinant baculovirus and then left for 7 days at 5° C. so that the pupae were completely infected with the virus.

After infection, the silkworm pupae were disrupted in a buffer with a homogenizer. A solution obtained by disruption was filtered and centrifuged to remove solid materials. In the process of from insertion of the bovine tissue factor cDNA into baculovirus to removal of solid materials, "Superworm" service available from Katakura Industries Co., Ltd. was utilized.

The solution from which solid materials had been removed was obtained from Katakura Industries Co., Ltd. This solution was further homogenized with a homogenizer (As One Corporation, 10 strokes at a revolution number of 5000 rpm) and centrifuged (3000×g, 8° C., 10 minutes). Then, the supernatant was obtained, and 2 parts by volume of 10% surfactant NP-40 (Calbiochem Inc.) were added to 8 parts by volume of the supernatant. The final concentration of the surfactant NP-40 in the resulting mixture was 2%. Then, the mixture was incubated at 30° C. for 3 hours thereby inactivating the baculovirus and solubilizing the recombinant bovine tissue factor.

The inactivation of the baculovirus was confirmed by examining the virus titer of the mixture by observing the presence or absence of viral infection under a microscope according to a Reed-Muench method (Reed, L. J. and Muench, H.: Amer. J. Hyg., 27, 493 (1938)).

The mixture was centrifuged (3000×g, 8° C., 30 minutes) to obtain a supernatant from which lipoprotein and lipid fractions had been removed. Then, the resultant supernatant was introduced into a cellulose tube for dialysis (Sanko Junyaku Co., Ltd.) and dialyzed against 20 mM HEPES, pH 7.2, containing 150 mM sodium chloride. After dialysis, the solution in the dialysis tube was obtained. The obtained solution used as rTF-containing solution SW. The rTF-containing solution SW contains the recombinant bovine tissue factor and silkworm-derived soluble components.

Production of Recombinant Bovine Tissue Factor by Sf9 as Host

A bovine cerebrum cDNA library (Stratagene Corporation) was obtained, and on the basis of the method described in the literature of Yuko Takayenoki et al. supra, a gene of bovine tissue factor was amplified by PCR. A full-length bovine tissue factor-coding gene encoding a soluble domain and transmembrane domain of bovine tissue factor was cloned. In PCR amplification, a primer having a BgmHI cleavage site (5'-ggatccatggcgacccccaacgggccccg (SEQ ID NO: 5)) was used as the forward primer, and a primer having an XhoI cleavage site (5'-ctcgagttatgcagcgttgagcggcgtg (SEQ ID NO:6)) was used as the backward primer. The cloned gene could be confirmed to be a DNA encoding a protein represented by SEQ ID NO: 2 by examining its nucleotide sequence with a 4000L DNA sequencer (LI-COR Inc.).

The cloned cDNA was digested with BamHI and XhoI and then inserted into a transfer vector pFast Bac (GIBCO BRL). *Escherichia coli* DH10 Bac containing baculovirus genomic DNA was transfected with the pFast Bac. Finally, the baculovirus into which the bovine tissue factor cDNA had been introduced was obtained. Cultured insect cell Sf9 was transfected with the recombinant baculovirus and then cultured for 72 hours to give P1 virus. Then, other Sf9 was infected with the P1 virus and then cultured for 4 days in Grace Medium (Invitrogen Corporation) containing 10% FBS, whereby P2 virus was obtained. Other Sf9 was infected with the resulting P2 virus, and the infected Sf9 was cultured in Sf-900II Serum Free Medium (Invitrogen Corporation). After culture, Sf9 was collected. From the collected Sf9, a recombinant bovine tissue factor was extracted with a Tris buffer, pH 7.5, containing 1% CHAPS, thereby preparing a rTF-containing solution SF. The rTF-containing solution SF contains the recombinant bovine tissue factor and Sf9 cell-derived soluble components.

SDS-PAGE of the rTF-Containing Solutions

The rTF-containing solution SW and the rTF-containing solution SF obtained by the preparation method described above were subjected to SDS-PAGE (sodium dodecyl sulfate-polyacrylamide gel electrophoresis).

10 μL of an SDS sample buffer, pH 7.5, containing 200 mM Tris, 72 mM glycine and 0.02% SDS was added to 10 μL of the rTF-containing solution SW. The resulting mixture was boiled at 100° C. for 5 minutes to prepare a sample for SDS (sample SW for SDS).

10 μL of the resulting sample SW for SDS was put to a well of 5 to 10% gradient polyacrylamide gel and electrophoresed at 50 V for 3 hours in an electrophoresis chamber (Mini Protein II Electrophoresis Unit, Nippon Bio-Rad Laboratories K.K.). After electrophoresis, the polyacrylamide gel was stained by using a silver staining kit (Daiichi Pure Chemicals Co., Ltd.). The results are shown in FIG. 1. In the electrophoresis profile in FIG. 1, lane 1 is a molecular-weight marker (Precision Plus, Nippon Bio-Rad Laboratories K.K.), and lane 2 is the sample SW for SDS. The position in which a band of the recombinant bovine tissue factor appeared (position with a molecular weight of about 40 kDa) was indicated by an arrow.

10 μL of a 2×SDS sample buffer, pH 7.5, containing 200 mM Tris, 72 mM glycine and 0.02% SDS was added to 10 μL of the recombinant bovine tissue factor-containing solution SF. The resulting mixture was boiled at 100° C. for 5 minutes to prepare a sample for SDS (sample SF for SDS).

Figure 2:
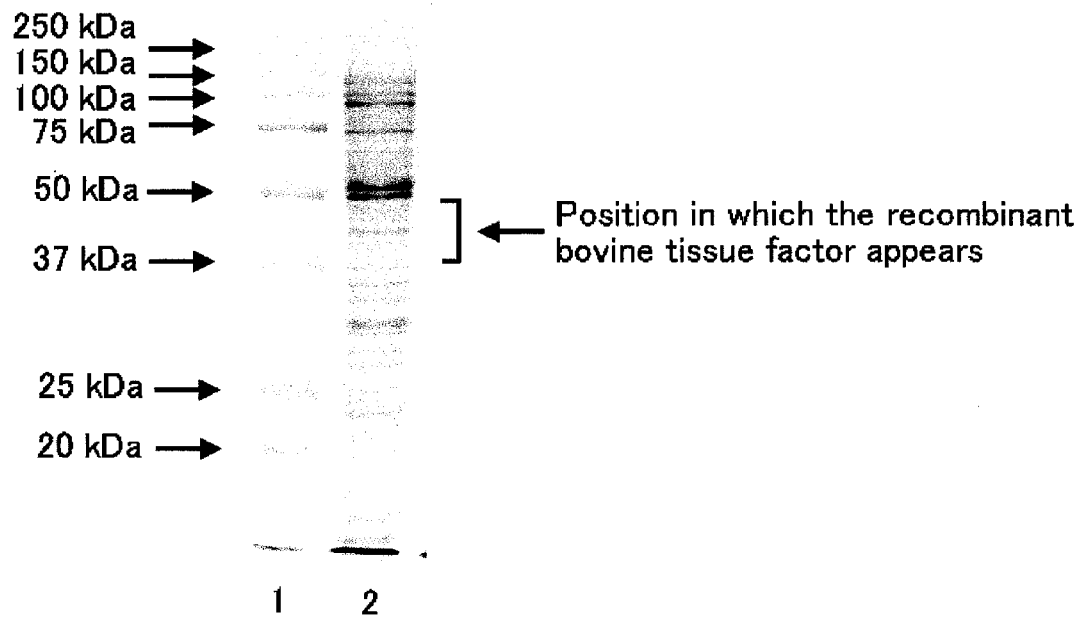
FIG. 2 shows SDS-PAGE results of a recombinant bovine tissue factor-containing solution SF.

10 μL of the resulting sample SF for SDS was put to a well of 5 to 10% gradient polyacrylamide gel and electrophoresed at 100 V for 1 hour in an electrophoresis chamber (Mini Protein II Electrophoresis Unit, Nippon Bio-Rad Laboratories K.K.). After electrophoresis, the polyacrylamide gel was stained by using a CCB staining kit (Wako Pure Chemical Industries, Ltd.) The results are shown in FIG. 2. In the electrophoresis profile in FIG. 2, lane 1 is a molecular-weight marker (Precision Plus, Nippon Bio-Rad Laboratories K.K.), and lane 2 is the sample SF for SDS. The position in which a band of the recombinant bovine tissue factor appeared (position with a molecular weight of about 40 kDa) was indicated by an arrow.

From the results in FIGS. 1 and 2, it was found that the rTF-containing solution SW and the rTF-containing solution SF contain not only the recombinant bovine tissue factors but also a very large number of proteins derived from the hosts.

From the results in FIG. 1, it can be thought that the purity of the recombinant bovine tissue factor in the rTF-containing solution SW is about 5 to 10%.

From the results in FIG. 2, it can be thought that the purity of the recombinant bovine tissue factor in the rTF-containing solution SF is about 1 to 5%.

Preparation of rTF-PL Complex 0.4 g of basis soybean lecithin (Nisshin Oil Mills, Ltd.) was dissolved in 0.25% sodium deoxycholate DOC (20 mL). The basis soybean lecithin was completely dissolved at room temperature with a rotator and the mixture was obtained. 0.1 g of 1,2-oleyl-sn-glycero-3-phosphoethanolamine (DOPE) and 0.3 g of 1,2-dioleyl-sn-glycero-3-phospho-L-serine (DOPS) (both available from Avanti polar lipid. Inc.) were suspended in the mixture to prepare a phospholipid solution.

To 37.5 mL of the phospholipid solution were added 5 mL of 0.5 M nickel chloride solution, 5.0 mL of 10 mM HEPES buffer, pH 7.3, and 2.5 mL of the above rTF-containing solution (the rTF-containing solution SW or the rTF-containing solution SF). The mixture thus obtained was stirred for 30 seconds with a vortex. After stirring, the mixture was reacted at 37° C. for 15 minutes in a BRANSON #2210-type ultrasonic device and then left at 37° C. for 1 hour. The mixture was transferred into a dialysis membrane (cellulose tube for dialysis, Sanko Junyaku Co., Ltd.) and dialyzed 3 times against 10 mM HEPES, pH 7.3, containing 0.15 M sodium chloride. After dialysis, the solution in the dialysis tube was obtained. The obtained solution was used as a rTF-PL complex-containing solution (a rTF-PL complex-containing solution SW or a rTF-PL complex-containing solution SF). The rTF-PL complex-containing solution SW contains silkworm-derived soluble components and the complex of recombinant bovine tissue factor and phospholipid. The rTF-PL complex-containing solution SF contains Sf9 cell-derived soluble components and the complex of recombinant bovine tissue factor and phospholipid.

Preparation of Reagent for Thrombo-Test (1) Preparation of Barium Sulfate-Adsorbed Plasma To bovine plasma supplemented with citric acid were added barium sulfate in an amount of 30 w/v % based on the bovine plasma and physiological saline in an amount of 20 v/v % based on the bovine plasma, and the mixture was stirred for 60 minutes with a rotator.

The mixture was centrifuged at 5000 rpm, 4° C., for 15 minutes, and then a supernatant was obtained. To this supernatant was little by little added barium sulfate in an amount of 30 w/v % based on the supernatant. In this way, factors II, VII, IX and X in the plasma were adsorbed onto barium sulfate. Thereafter, the sample was centrifuged to obtain a supernatant. The supernatant was introduced into a dialysis tube (cellulose tube for dialysis, Sanko Junyaku Co., Ltd.) and dialyzed at 2 to 8° C. against physiological saline as an external solution. After dialysis, the solution in the dialysis tube was filtered through a 0.45-μm filter. The resulting filtrate was used as barium sulfate-adsorbed plasma, to prepare the following reagents.

(2) Preparation of Reagents for Thrombo-Test

The rTF-PL complex-containing solution and the barium sulfate-adsorbed plasma as prepared described above and 40 mM HEPES buffer, pH 7.3 containing 4 mM calcium lactate were mixed under stirring in a ratio of 1:2:1 to prepare a reagent for thrombo-test. A reagent for thrombo-test, prepared from the rTF-PL complex-containing solution SW, was used as reagent SW A reagent for thrombo-test, prepared from the rTF-PL complex-containing solution SF, was used as reagent SF.

Example 1

Influence of Silkworm-Derived Soluble Components on Coagulation Activity

According to the preparation method described above, the reagent SW was prepared in triplicate (SW-1, SW-2 and SW-3).

According to the preparation method described above, a reagent SW for thrombo-test was prepared from silkworm pupae uninfected with baculovirus. This reagent was used as reagent SW (uninfected). The reagent SW (uninfected) contains soluble components derived from the silkworm, but does not contain the recombinant bovine tissue factor and baculovirus-derived soluble components.

Separately, silkworm pupae were infected with baculovirus in which the bovine tissue factor cDNA had not integrated, and from the infected silkworm pupae, a reagent SW for thrombo-test was prepared according to the preparation method described above. This reagent was used as reagent SW (cDNA-free). The reagent SW (cDNA-free) contains soluble components derived from the silkworm and from the baculovirus, but does not contain the recombinant bovine tissue factor.

These 5 reagents (SW-1, SW-2, SW-3, SW (uninfected), and SW (cDNA-free)) were used to measure the coagulation time of normal plasma with a fully automatic blood coagulation analyzer Coagrex 800 (Shimadzu Corporation). Separately, the 5 reagents were diluted 2-, 4- and 8-fold with physiological saline respectively. These diluted reagents were used to measure the coagulation time of normal plasma in the same manner as above. As the normal plasma, Coagutrol N (Sysmex Corporation) was used. The results of coagulation time (seconds) obtained with each reagent are shown in Table 1.

TABLE 1

|  | Coagulation Time (seconds) | | | |
| --- | --- | --- | --- | --- |
|  | 1-fold dilution | 2-fold dilution | 4-fold dilution | 8-fold dilution |
| SW (uninfected) | ND | ND | ND | ND |
| SW (cDNA-free) | ND | ND | ND | ND |
| SW-1 (0.27 mg/mL) | 31.3 | 35.7 | 45.1 | 53.8 |
| SW-2 (0.41 mg/mL) | 30.4 | 33.6 | 40.8 | 48.8 |
| SW-3 (0.46 mg/mL) | 32.3 | 39.6 | 47.4 | 55.1 |

In Table 1, the coagulation time was not detected when the reagent SW (uninfected) or the reagent SW (cDNA-free) was used. On the other hand, the coagulation time was detected when the reagent SW-1, SW-2 or SW-3 was used. From this result, it was found that silkworm- and baculovirus-derived soluble components contained in the reagent do not induce blood coagulation reaction.

When the reagent SW-1, SW-2 or SW-3 was used, the coagulation time was prolonged as the dilution ratio was increased. When the dilution ratio of the reagent is increased, the concentration of the recombinant bovine tissue factor in the reagent is decreased. It could accordingly be confirmed that there is correlation between the concentration change of the recombinant bovine tissue factor in the reagent and the coagulation time.

From the foregoing, it was found that silkworm- and baculovirus-derived soluble components contained in the reagent do not exert any influence on the coagulation reaction of blood. Hence, it was found that the purification of the recombinant tissue factor to remove these soluble components is not necessary for preparation of the reagent for measuring clotting time. Further, it can be thought that when cultured insect cells such as Sf9 are used as the host, soluble components derived from the host do not exert any influence on the coagulation reaction of blood either.

Example 2

Sensitivity of Reagent SW and Reagent SF

The reagents SW and SF prepared by the method described above were used to measure the coagulation time and international standard index (ISI value) of four AK Calibrants (AK-Aa, AK-Bb, AK-Cc and AK-Dd, all of which are manufactured by Immuno Inc., Austria) with a fully automatic blood coagulation analyzer Coagrex 800 (Shimadzu Corporation). AK Calibrants are those with INR indicated values determined previously in EQUSTA Surveysance.

As control reagent I, a commercial thrombo-test reagent (Fukugou-Inshi T "Kokusai", Sysmex Corporation) of known calculated ISI value was used to measure the coagulation time and ISI values of the AK Calibrants in the same manner as described above. The commercial reagent is a reagent for thrombo-test which contains native bovine cerebrum thromboplastin as the bovine tissue factor-phospholipid complex.

As control reagent II, a reagent for thrombo-test, which contained the purified recombinant bovine tissue factor, was prepared. The control reagent II was used to measure the coagulation time (seconds) and ISI values of AK Calibrants in the same manner as described above. The control reagent II was prepared in the same manner as for the reagent SW except that ammonium sulfate fractionation was carried out in the step of preparing the reagent SW, thereby providing about 95% or more purity for the recombinant bovine tissue factor contained in the rTF-containing solution SW. The reagent SW, the reagent SF and the control reagent II were prepared such that similar coagulation time to that of the control reagent I was used when Coagutrol N (Sysmex Corporation) was measured.

The coagulation time (seconds) and ISI value obtained by using each reagent are shown in Table 2.

TABLE 2

| | Coagulation Time (seconds) | | | |
|---|---|---|---|---|
| | Reagent SW | Reagent SF | Control reagent I | Control reagent II |
| AK-A | 35.0 | 39.1 | 34.1 | 33.9 |
| AK-B | 59.9 | 64.2 | 55.3 | 56.4 |

TABLE 2-continued

| | Coagulation Time (seconds) | | | |
|---|---|---|---|---|
| | Reagent SW | Reagent SF | Control reagent I | Control reagent II |
| AK-C | 106.1 | 106.6 | 88.6 | 95.4 |
| AK-R | 110.5 | 112.0 | 90.4 | 100.6 |
| AK-D | 177.8 | 179.3 | 133.5 | 156.9 |
| ISI value | 0.99 | 0.97 | 0.91 | 0.90 |

From the results in Table 2, it could be confirmed that for Calibrants AK-Aa to AK-Dd, the reagents SW and SF exhibit similar coagulation time and sensitivity to those of the control reagents I and II. From this result, it was found that both the reagents SW and SF exhibit coagulation time and sensitivity similar to those achieved by the conventional reagent using native bovine cerebrum thromboplastin and the reagent containing the purified recombinant bovine tissue factor.

Example 3

Correlation in Coagulation Activity between Reagent SW or SF and Control Reagents The same reagents (reagent SW, reagent SF, control reagent I and control reagent II) as used in Example 2 were used to measure the coagulation activity (%) of plasmas (N=20) from patients who had received warfarin, with a fully automatic blood coagulation analyzer Coagrex 800 (Shimadzu Corporation). A calibration curve for determining the activity (%) was prepared using Coagutrol N (Sysmex Corporation). As the plasmas from patients who had received warfarin, Multi-Coumadin Set (Georoge King Biomedical Inc.) was used.

The activity (%) obtained with each reagent is shown in Table 3.

TABLE 3

| | Coagulation Activity (%) | | | |
|---|---|---|---|---|
| Sample No. | Reagent SW | Reagent SF | Control reagent I | Control reagent II |
| 1 | 12.1 | 11.9 | 12.1 | 9.7 |
| 2 | 22.7 | 24.6 | 23.8 | 24.9 |
| 3 | 32.8 | 34.4 | 33.6 | 34.6 |
| 4 | 14.3 | 14.3 | 14.5 | 10.8 |
| 5 | 75.3 | 79.9 | 74.7 | 76.9 |
| 6 | 38.0 | 37.8 | 37.8 | 37.4 |
| 7 | 42.5 | 39.4 | 40.3 | 44.2 |
| 8 | 100.2 | 104.3 | 98.3 | 108.0 |
| 9 | 128.0 | 123.1 | 129.9 | 120.9 |
| 10 | 95.5 | 98.5 | 95.7 | 100.5 |
| 11 | 7.2 | 6.8 | 6.6 | 7.0 |
| 12 | 14.7 | 15.0 | 15.0 | 14.3 |
| 13 | 9.5 | 9.6 | 9.6 | 10.1 |
| 14 | 13.7 | 14.1 | 13.9 | 12.7 |
| 15 | 128.0 | 123.1 | 129.9 | 131.8 |
| 16 | 95.5 | 98.5 | 95.7 | 99.5 |
| 17 | 6.9 | 6.9 | 6.8 | 7.1 |
| 18 | 14.7 | 15.0 | 15.0 | 14.2 |
| 19 | 9.5 | 9.6 | 9.6 | 9.7 |
| 20 | 13.7 | 14.1 | 13.9 | 13.0 |

From the results in Table 3, it could be confirmed that for each plasma sample, the reagents SW and SF show similar activity to that by the control reagents I and II. From this result, it was found that the reagents SW and SF show similar activity to that by the conventional reagent using native bovine cerebrum thromboplastin and the reagent containing the purified recombinant bovine tissue factor.

Figure 4:
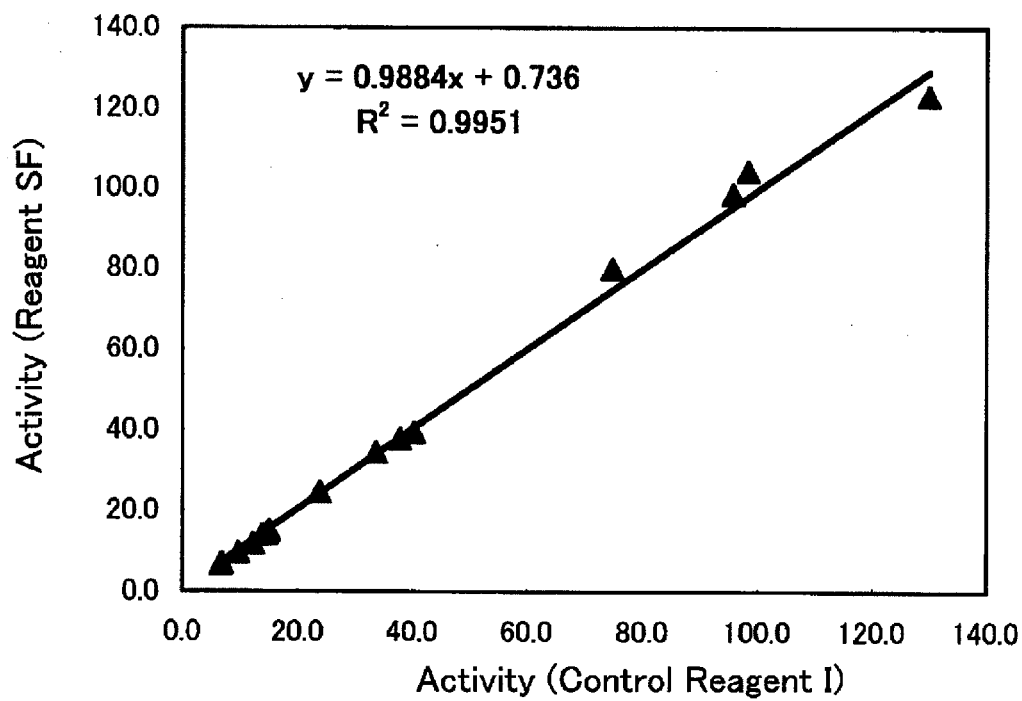
FIG. 4 is a graph showing the relationship between the activity of a control reagent I and the activity of a reagent SF.

The correlation between the activity attained by the control reagent I and the activity by the reagent SW for each blood sample is shown in FIG. 3. The correlation between the activity attained by the control reagent I and the activity by the reagent SF for each blood sample is shown in FIG. 4. In FIG. 3, the activity (%) determined by the control reagent I is shown on the abscissa, and the activity (%) by the reagent SW is shown on the ordinate. In FIG. 4, the activity (%) determined by the control reagent I is shown on the abscissa, and the activity (%) by the reagent SF is shown on the ordinate.

As is evident from FIGS. 3 and 4, it was found that both the activity (%) by the reagent SW and the activity (%) by the reagent SF are highly correlated with the activity (%) by the control reagent I. From this result, it was found that the activity by the reagents SW and SF in this example is comparable to that of the conventional reagent using native bovine cerebrum thromboplastin.

Example 4

Sensitivity, to PIVKA, of Reagent for Thrombo-Test

The rTF-containing solution SW was used to examine the sensitivity thereof to PIVKA.

Specifically, the reagent SW for thrombo-test and 20 mM calcium chloride solution were mixed with each other in equal amounts. The resulting mixture was mixed with human adsorbed plasma to prepare a reagent for PIVKA sensitivity test.

Separately, a bovine cerebrum-derived thromboplastin solution and a rabbit brain-derived thromboplastin solution were used to prepare control reagents for PIVKA sensitivity test in the same manner as described above. The bovine cerebrum-derived thromboplastin solution contained thromboplastin extracted from a bovine cerebrum. The rabbit brain-derived thromboplastin solution contained thromboplastin extracted from a rabbit brain.

The prepared reagents for PIVKA sensitivity test were used to measure the coagulation time of normal plasma and 3 plasmas from patients who had received warfarin, with a fully automatic blood coagulation analyzer Coagrex 800 (Shimadzu Corporation).

As the normal plasma, Coagutrol N (Sysmex Corporation) and dilutions thereof with physiological saline were used. For preparing such dilutions, Coagutrol N was diluted 3-, 5- and 7-fold respectively.

As the plasmas from patients who had received warfarin, Multi-Coumadin Set (Georoge King Biomedical Inc.) and dilutions thereof with physiological saline were used. For preparing such dilutions, the plasmas were diluted 2-, 3- and 5-fold respectively.

The results are shown in FIG. 5.

Figure 5A:
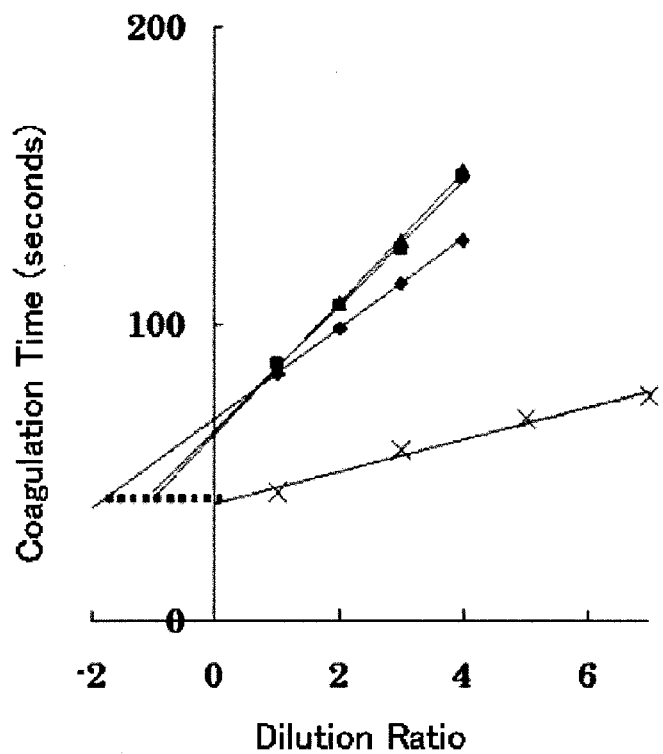
FIGS. 5A-5C are graphs showing the relationship between the dilution ratio of plasma and coagulation time, in measurement using a reagent for PIVKA sensitivity test prepared in the Example 4.
Figure 5B:
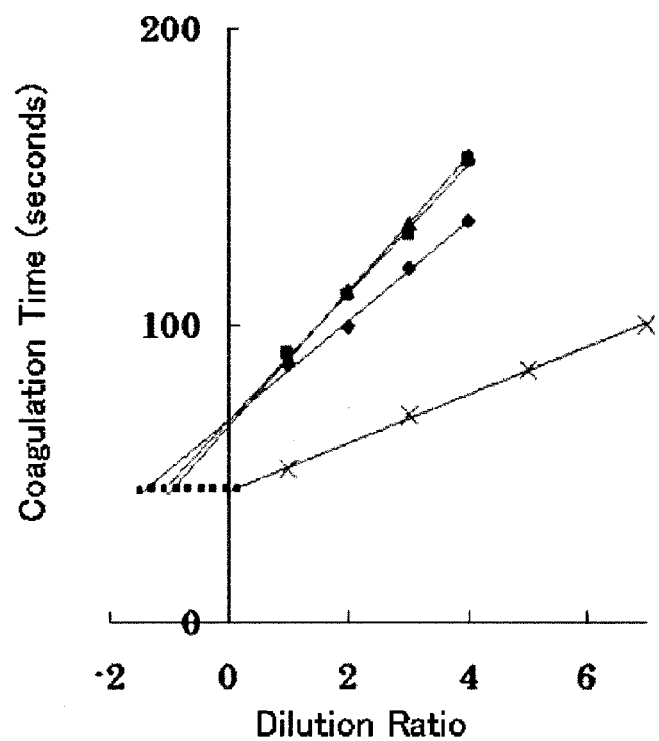
Figure 5C:
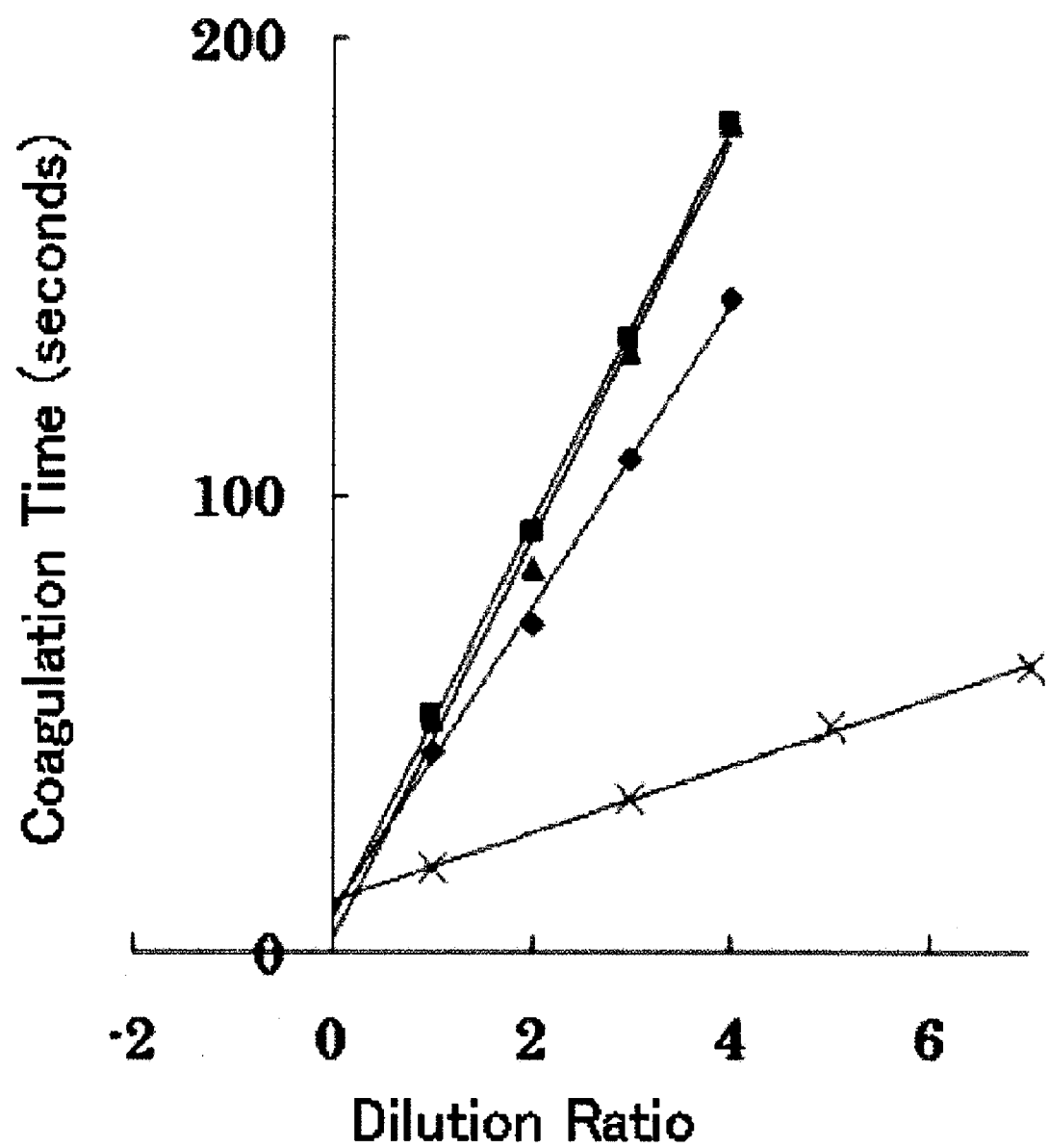

FIG. 5A shows the results obtained by using the rTF-containing solution SW. FIG. 5B shows the results obtained by using the bovine cerebrum-derived thromboplastin solution. FIG. 5C shows the results obtained by using the rabbit brain-derived thromboplastin solution. In FIG. 5, the coagulation time (seconds) is shown on the ordinate, and the dilution ratio of plasma is shown on the abscissa. The sensitivity to PIVKA was examined according to the method of Hemker and Denson.

According to the method of Hemker and Denson, a straight line indicated by the normal plasma was compared with a straight line indicated by the plasma from patients. When the bovine cerebrum-derived thromboplastin solution was used (FIG. 5B), coagulation inhibition (dotted line) by PIVKA was observed in the plasma from patients who had received warfarin. On the other hand, when the rabbit brain-derived thromboplastin solution was used (FIG. 5C), coagulation inhibition (dotted line) by PIVKA was not observed. Accordingly, it can be said that the native bovine thromboplastin is sensitive to PIVKA, while the native rabbit thromboplastin is low in sensitivity to PIVKA. These results were in accordance with those in the report of Hemker and Denson.

When the reagent SW for thrombo-test was used (FIG. 5A), results similar to those (FIG. 5B) of the bovine cerebrum-derived thromboplastin solution were obtained. From these results, it could be confirmed that the complex of recombinant bovine tissue factor and phospholipid in the reagent in this example shows similar properties to that of native bovine thromboplastin. It was further found that silkworm-derived soluble components contained in the reagent SW for thrombo-test does not exert any influence on sensitivity to PIVKA.

From the results in the Examples above, it was found that the above reagents for measuring clotting time, though containing soluble components derived from an insect or a cultured insect cell, show sensitivity and coagulation activity at the same level as those of the conventional reagents for measuring clotting time. From this result, it was found that the above reagent for measuring clotting time can be used as a substitute for the conventional reagent for measuring clotting time. Further, the recombinant tissue factor used in the above reagent for measuring clotting time can simplify the purification process so that as compared with measuring clotting time methods using the conventional recombinant tissue factor, productivity can be increased and production costs can be reduced.

What is claimed is:

1. A reagent for measuring clotting time, comprising a complex of phospholipid and recombinant tissue factor formed by mixing the phospholipid with a solution comprising the recombinant tissue factor, wherein the tissue factor is obtained by a process comprising disrupting infected silkworm or infected cultured silkworm cells in a buffer with a homogenizer, wherein the infected silkworm or the infected cultured silkworm cells express the recombinant tissue factor, wherein water insoluble materials are removed from the solution; and wherein the recombinant tissue factor has at least 95% sequence identity to the amino acid sequence of SEQ ID NO: 1.

2. The reagent of claim 1, wherein the recombinant tissue factor is a recombinant bovine tissue factor comprising a soluble domain and a transmembrane domain.

3. The reagent of claim 1, wherein the reagent is a thrombo-test reagent, a hepaplastin test reagent or a prothrombin time reagent.

4. The reagent of claim 1, further comprising a Factor I, a Factor V, a barium sulfate-adsorbed plasma, a calcium ion, or a mixture thereof.

5. The reagent of claim 2, further comprising at least one component selected from the group consisting of a Factor I, a Factor V, a barium sulfate-adsorbed plasma and a calcium ion.

6. The reagent of claim 1, wherein the process comprises:
    integrating a tissue factor cDNA in a baculovirus DNA to express a recombinant tissue factor in said silkworm or cultured silkworm cells.

7. The reagent of claim 6, wherein the cDNA encodes a soluble domain and transmembrane domain of bovine tissue factor.

8. The reagent of claim 6, wherein the cDNA encodes a recombinant tissue factor having at least 95% sequence identity with the amino acid sequence of SEQ ID NO: 2.

9. The reagent of claim 6, wherein the solution comprises a surfactant.

10. The reagent of claim 6, wherein the reagent is a thrombo-test, a reagent for hepaplastin test or a prothrombin time reagent.

11. A method of manufacturing a reagent for measuring clotting time comprising:
    infecting silkworm or cultured silkworm cells with a recombinant baculovirus comprising an integrated tissue factor cDNA;
    disrupting infected silkworm or infected cultured silkworm cells that express tissue factor in said silkworm or cultured silkworm cells, wherein the cells are disrupted in a buffer with a homogenizer to obtain the tissue factor; and
    mixing phospholipids with a solution comprising the tissue factor, wherein the tissue factor has at least 95% sequence identity to the amino acid sequence of SEQ ID NO:1.

* * * * *